United States Patent [19]
Hsieh

[11] Patent Number: 5,812,628
[45] Date of Patent: Sep. 22, 1998

[54] METHODS AND APPARATUS FOR DETECTING PARTIAL VOLUME IMAGE ARTIFACTS

[75] Inventor: Jiang Hsieh, Waukesha, Wis.

[73] Assignee: General Electric Company, Milwaukee, Wis.

[21] Appl. No.: 763,928

[22] Filed: Dec. 12, 1996

[51] Int. Cl.⁶ .......................................... A61B 6/03
[52] U.S. Cl. ................................. 378/8; 378/901
[58] Field of Search ..................... 378/4, 8, 901

[56] References Cited

U.S. PATENT DOCUMENTS 5,412,703  5/1995  Goodenough et al. ............... 378/8

Primary Examiner—David P. Porta
Assistant Examiner—David Vernon Bruce
Attorney, Agent, or Firm—John S. Beulick; John H. Pilarski

[57] ABSTRACT

The present invention, in one form, is a method for detecting a partial volume artifact in scan data acquired during a tomographic scan. In accordance with one embodiment of the algorithm, an object of interest is scanned to generate scan data. Sampling pairs of the scan data are identified and used to generate an inconsistency map. The inconsistency map is weighted and filtered to generate a partial volume signature which identifies partial volume artifacts.

20 Claims, 2 Drawing Sheets

METHODS AND APPARATUS FOR DETECTING PARTIAL VOLUME IMAGE ARTIFACTS

FIELD OF THE INVENTION

This invention relates generally to computed tomography (CT) imaging and more particularly, to detecting partial volume image artifacts in an image reconstructed from scan data.

BACKGROUND OF THE INVENTION

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object.

One method for reconstructing an image from a set of projection data is referred to in the art as the filtered backprojection technique. This process converts the attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed. In addition to reduced scanning time, helical scanning provides other advantages such as improved image quality and better control of contrast.

In helical scanning, and as explained above, only one view of data is collected at each slice location. To reconstruct an image of a slice, the other view data for the slice is generated based on the data collected for other views. Helical reconstruction algorithms are known, and described, for example, in C. Crawford and K. King, "Computed Tomography Scanning with Simultaneous Patient Translation," Med. Phys. 17(6), Nov/Dec 1990.

During scanning, the x-ray beam is known to spread along a z-axis to form a "scanning plane". For each image slice, the object to be imaged often only partially intrudes into the scanning plane. Specifically, the object is only partially subjected to the x-ray beam, thus causing inconsistencies in the projection data. When reconstructing an image for a particular slice, these inconsistencies generate incorrect CT numbers, streaks, and other artifacts in generated images. As the slice thickness is increased, the likelihood of partial intrusion increases. The image errors created by partial intrusion are often referred to as "partial volume artifacts".

To reduce partial volume artifacts, operators typically must select slices of sufficiently small thickness to ensure constant attenuation characteristics across the slice, i.e., to ensure that the object does not partially intrude on the scan plane. However, thin slices typically require significantly long scanning times and x-ray tube cooling delays. Conversely, thicker slices are preferred for improving x-ray photon flux. Therefore, it is desirable to reduce partial volume artifacts in thicker slices.

Another known method of reducing partial volume artifacts includes altering x-ray source collimators during a scan. For example, a 10 mm collimator which provides a slice thickness of 10 mm may be used when scanning a region with few bony structures. However, when scanning a region with multiple bony structures, a 3 mm collimator which provides a slice thickness of 3 mm, may be used. This method is both time consuming and cumbersome. Furthermore, this method is neither practical nor efficient when scanning adjacent differing regions.

Neither of the above-mentioned methods automatically identify the presence of the partial volume artifact. Rather, each method requires a human operator to either identify the partial volume artifact in the displayed image, or to take preventive measures to avoid the artifact. This operator involvement is a tedious and time consuming process, and is only as reliable as the operator. In many cases, the operator could either be overly cautious in prescribing thin slices or be careless in image quality and scan partial volume regions with thicker slices.

Accordingly, it would be desirable to automatically detect partial volume artifacts without operator intervention. It also would be desirable to provide such detection without compromising CT system efficiency.

SUMMARY OF THE INVENTION

These and other objects may be attained by methods and apparatus which automatically detect the presence of partial volume artifacts. Particularly, and in accordance with one embodiment of the present invention, the object is scanned to generate projection data for the object. Sampling pairs of projection data are then identified so that the projection data in each such sampling pair is generated from x-ray beams projected 180° apart along the same path. The projection data in the identified sampling pairs is then used to generate an inconsistency map, which includes differences between the projection data in each sampling pair. The inconsistency map is used to determine a partial volume signature which is representative of partial volume artifacts in the projection data.

Using the above-described algorithm, partial volume artifacts are detected without reducing CT system efficiency. In addition, the image resolution is maintained.

DETAILED DESCRIPTION OF THE DRAWINGS

Figure 1:
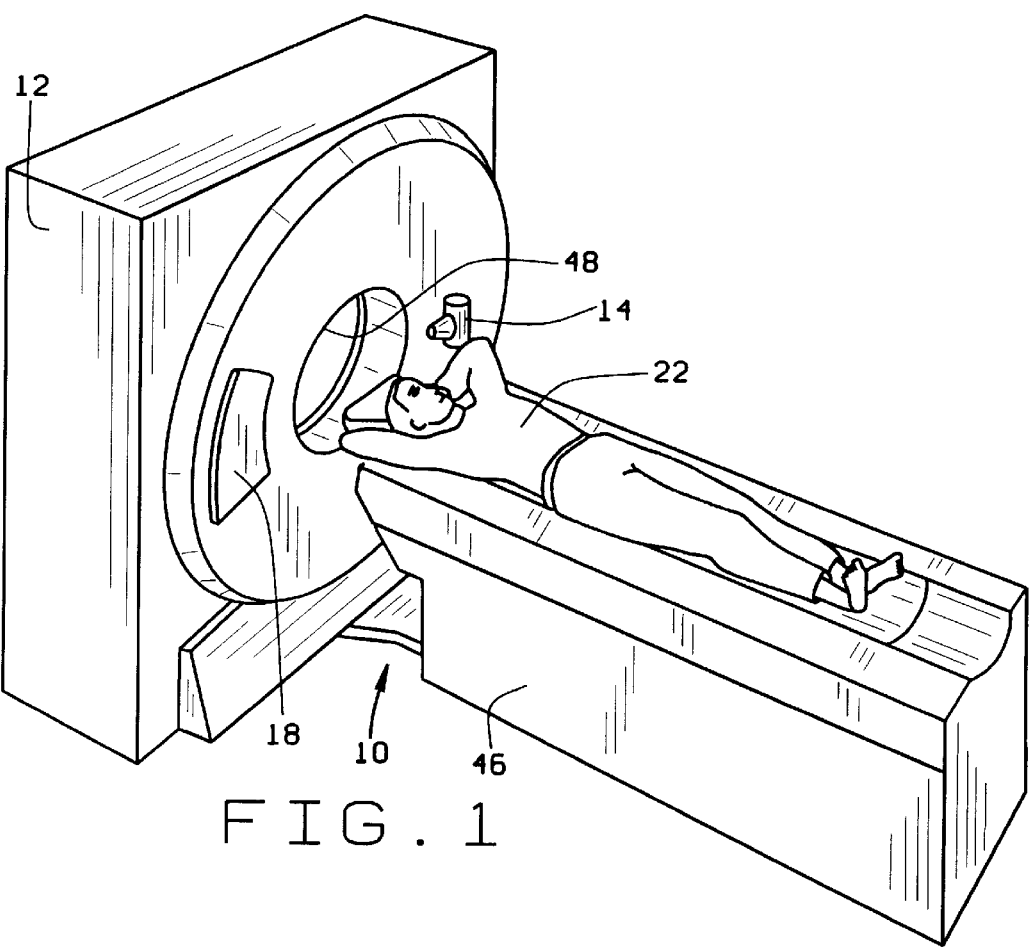
FIG. 1 is a pictorial view of a CT imaging system.
Figure 2:
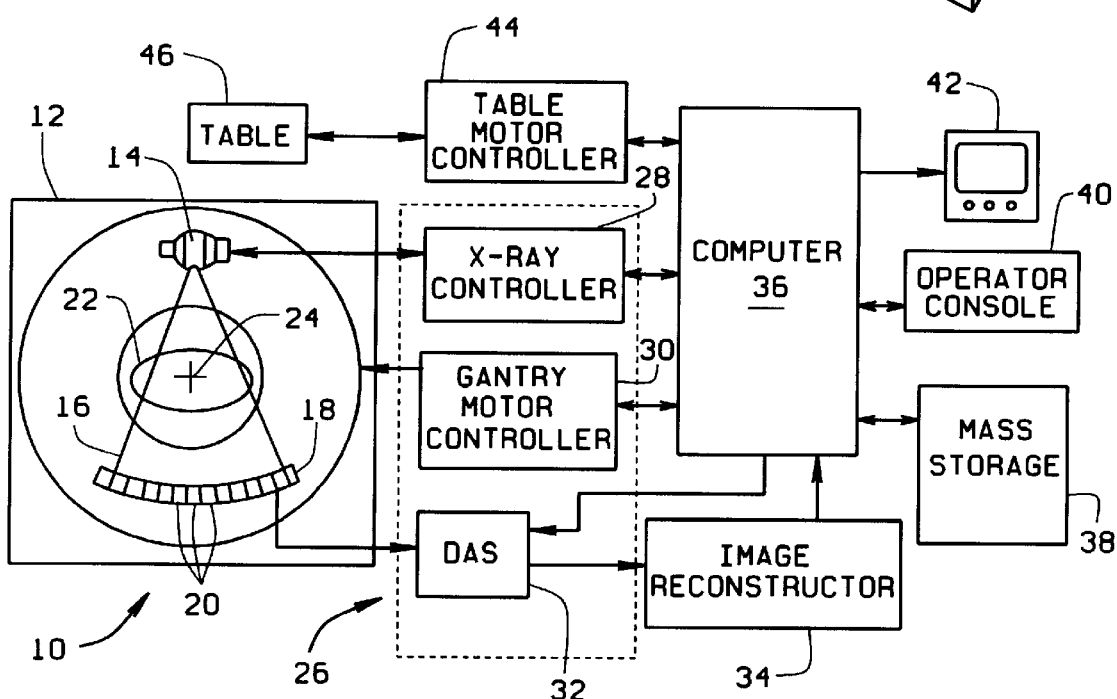
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. X-ray beam is collimated by a collimator (not shown) to lie within in an X-Y plane of a Cartesian coordinate system and generally referred to as an "imaging plane". Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

The following discussion which describes detecting partial volume image artifacts sometimes refers specifically to an axial scan. The artifact reduction algorithm, however, is not limited to practice in connection with only axial scans, and may be used with other scans, such as helical scans. It should be further understood that the algorithm would be implemented in computer 36 and would process, for example, image data stored in mass storage 38. Other alternative implementations are, of course, possible.

Figure 3:
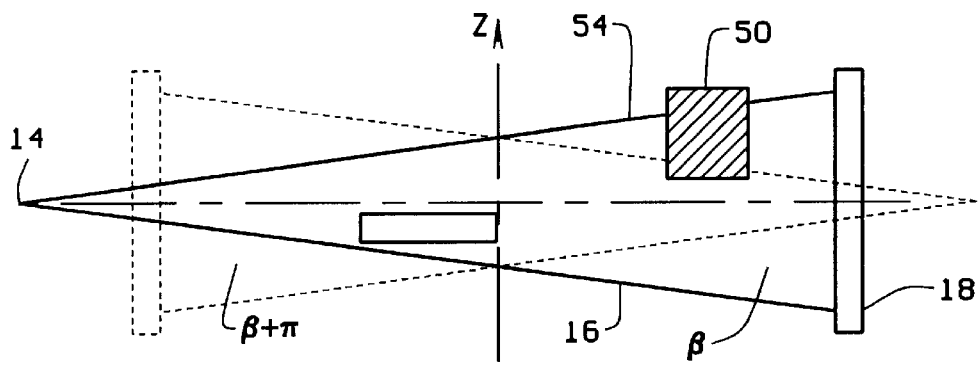
FIG. 3 is a schematic illustration of an x-ray source, a detector, and a partially intruded object of interest.

FIG. 3 is a schematic illustration of x-ray source 14, detector array 18, and a partially intruded object of interest 50. Object of interest 50 typically is a portion of patient 22 being scanned. X-ray source 14 projects x-ray beam 16 at a view angle β towards object of interest 50 and detector array 18. X-ray beam 16 typically diverges about an iso-center 52 along a z-direction to form a "scan plane" 54. The divergence of x-ray beam 16 impinging detector array 18 is referred to herein as "slice thickness".

As shown in FIG. 3, x-ray beam 16 only passes through a portion of object of interest 50, i.e., object of interest 50 "partially intrudes" on scan plane 54. As explained above, this partial intrusion causes errors and artifacts in slice images of object of interest 50. In addition, the extent of partial intrusion is angularly dependent. More specifically, the extent to which object of interest 50 intrudes in scan plane 54 is related to the distance between object 50 and x-ray source 14, i.e., the amount of intrusion is substantially linearly proportional to the distance between object 50 and x-ray source 14. For example, at an angle β+π, object of interest 50 is nearer to x-ray source 16, and thus a smaller portion of object of interest 50 partially intrudes scan plane 54 (shown in phantom in FIG. 3). Such angular dependence causes inconsistencies in projection data acquired during a scan of object of interest 50. More particularly, projection data, i.e., attenuation measurements, reflect different attenuation at different view angles β. These inconsistencies, as explained above, cause partial volume artifacts in resulting images of the object of interest, and the larger the inconsistencies, the more egregious the partial volume artifacts.

In accordance with one embodiment of the present invention, partial volume artifacts are detected by identifying inconsistencies in attenuation measurements. Particularly, projection data sampling pairs are identified to determine maximum inconsistencies in attenuation measurements for a scan of the object of interest. An inconsistency map is then generated using the maximum inconsistencies, and a partial volume signature of the scanned object of interest is identified. The partial volume signature, of course, is representative of partial volume artifacts.

Figure 4:
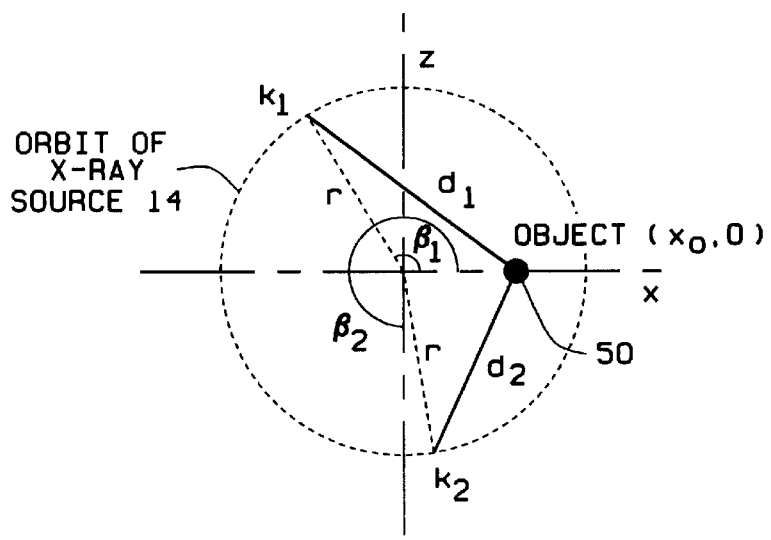
FIG. 4 is a schematic illustration of the trajectory of the x-ray source 14 about the object of interest shown in FIG. 3.

FIG. 4 is a schematic illustration of the trajectory of x-ray source 14 about object of interest 50 and iso-center 52. Specifically, x-ray source 14 is a distance r from iso-center 52 and rotates substantially circularly about iso-center 52. Object of interest 50 is located at a point $(x_0,0)$. At a first position $k_1$, x-ray source 14 is a distance $d_1$ from object of interest 50 and projects x-rays at a view angle $\beta_1$. At a second position $k_2$, x-ray source 14 is a distance $d_2$ from object of interest 50 and projects x-rays at a view angle $\beta_2$. The respective relationships between distances $d_1$ and $d_2$ and location $(x_0,)$ of object of interest 50 are expressed as:

$$\begin{cases} d_1^2 = r^2 + x_0^2 - 2x_0 r \cos(\beta_1) \\ d_2^2 = r^2 + x_0^2 - 2x_0 r \cos(\beta_2) \end{cases} \quad (1)$$

Maximum inconsistency in projection data, accordingly, occurs when $$\xi = |d_1^2 - d_2^2| = 2x_0 r |\cos(\beta_2) - \cos(\beta_1)| \quad (2)$$

is maximized. More particularly, and as described above, the amount of object 50 partial intrusion is substantially proportional to distances $d_1$ and $d_2$, respectively. Therefore, the inconsistency of projection data acquired at view angle $\beta_1$ and view angle $\beta_2$ is substantially proportional to the difference between distances $d_1$ and $d_2$. Such projection data inconsistency causes partial volume artifacts in a reconstructed image of object of interest 50.

From equation (2), it is shown that projection data inconsistency is maximized when $|\cos(\beta_2)-\cos(\beta_1)|=2$, i.e., $\beta_2=2k\pi$ and $\beta_1=(2k+1)\pi$, or $\beta_1=2k\pi$ and $\beta_2=(2k+1)\pi$, where k is an integer. Therefore, partial volume artifacts are detected in accordance with projection data acquired from two different x-ray beams projected 180°, or π, apart that extend through object of interest 50 and iso-center 54.

Sampling pairs of projection data are identified, or selected, so that the projection data of each such sampling pair is generated from x-ray beams projected 180° apart. More specifically, sampling pairs are identified in accordance with:

$$\beta_2 = \beta_1 + \pi + 2\gamma_1; \text{ and}$$

$$\gamma_2 = -\gamma_1 \quad (3)$$

where $\beta_1$ and $\beta_2$ are view angles for a first and second x-ray source 14 location, respectively, and $\gamma_1$ and $\gamma_2$ are detector angles for the first and second x-ray source 14 location, respectively.

Differences between the projection data of each sampling pair, as explained above, is proportional to the amount of partial intrusion. Accordingly, the greater the difference between projection data of a sampling pair, the greater the effects of partial intrusion.

An inconsistency map (IM) is generated using the projection data in the identified sampling pairs. Particularly, the differences between data in respective pairs are mapped for each detector channel, view angle and detector angle. Accordingly, when object of interest 50 does not partially intrude in the scan plane for a given detector angle and view angle, the IM indicates a value of zero, since the sampling pair represent the attenuation of the same object along the same path. The IM may be stored, for example, in computer 36.

The above described detection method is believed to efficiently and adequately detect partial intrusion, and thus partial intrusion artifacts, when one object of interest partially intrudes in the scan plane. However, if more than one object of interest intrudes in the scan plane, such method may not be sufficiently adequate. For example, if two objects of interest on opposite sides of iso-center 54 identically and partially intrude in the scan plane, then the IM from the projection data 180° apart will be zero.

Figure 5:
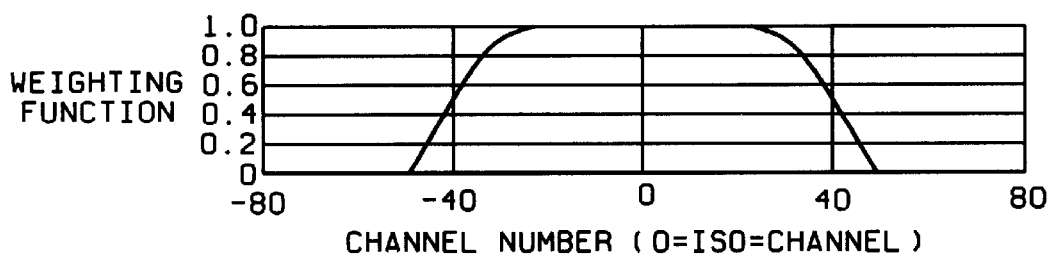
FIG. 5 illustrates a weighting function in accordance with one embodiment of the present invention.

To facilitate detecting partial intrusion when multiple objects of interest partially intrude, the IM is weighted by a weighting function to generate a weighted IM. Particularly, the IM is weighted on a view by view basis. The weighting function relates to the probability that the partially intruded object is of certain physical dimension. An example of a weighting function is shown in FIG. 5. The weighting function may be stored, for example, in computer 36.

To reduce any influence of statistical fluctuation of detector channels, the weighted IM is filtered, e.g., with a low pass filter, along the detector channel direction. Low pass filters are known in the art. The filtered IM is then used to determine an initial partial volume signature (PVS) curve of the object of interest. Specifically, a maximum amplitude for each view of the filtered IM is identified to indicate partial volume intrusion.

The initial partial volume signature also may be filtered to reduce influence of statistical fluctuation of detector channels. Specifically, the initial partial volume signature is low pass filtered along the view direction to generate a final partial volume signature, and the magnitude of the partial volume signature is used to detect partial volume artifacts. For example, if the final partial volume signature is substantially flat and small, then a reconstructed image will have substantially negligible partial volume artifacts. Conversely, if the final partial volume signature includes substantially large magnitudes at various view angles, then partial volume artifacts exist at such view angles.

The above-described method automatically detects partial volume intrusion and partial volume artifacts without requiring operator interference. The above-described method also does not significantly increase the costs of the CT system. Moreover, the method may be expanded to automatically vary slice thickness used during a scan. For example, the IM and partial volume signatures may be configured to generate a signal representative of potential partial volume artifacts to control mechanism 26 to change collimator apertures during a scan. If the IM and partial volume signatures indicate a large inconsistency, then the collimator aperture size is reduced. Alternatively, if the IM and partial volume signatures indicate a minimal inconsistency, then collimator aperture size is increased. The signal also may be transmitted to computer 36 so that a "warning" prompt appears on display 42 and operator may change collimator aperture sizes with console 40.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, although the CT system described herein is a "third generation" system, many other systems, such as "fourth generation" systems may be used. In addition, the algorithm described herein was implemented in connection with an axial scan, however the algorithm may also be implemented in connection with a helical scan. Furthermore, the algorithm described herein was implemented in connection with projection data, however the algorithm may also be implemented in connection with image data. Accordingly, the spirit and scope of the invention are to be limited only by the terms of the appended claims.

What is claimed is:

1. A method for detecting partial volume artifacts in scan data of an object, the scan data collected in a tomographic scan, said method comprising the steps of:

identifying at least one sampling pair of the scan data; and generating an inconsistency map using the identified sampling pair.

2. A method in accordance with claim 1 further comprising the step of weighting the generated inconsistency map.

3. A method in accordance with claim 2 further comprising the step of filtering the weighted inconsistency map to generate an initial partial volume signature.

4. A method in accordance with claim 3 wherein filtering the weighted inconsistency map comprises the step of low pass filtering the weighted inconsistency map along a channel direction.

5. A method in accordance with claim 3 further comprising the step of filtering the initial partial volume signature to generate a final partial volume signature.

6. A method in accordance with claim 5 wherein filtering the initial partial volume signature comprises the step of low pass filtering the initial partial volume signature along a view direction.

7. A method in accordance with claim 1 wherein the sampling pair is identified in accordance with:

$$\beta_2 = \beta_1 + \pi + 2\gamma_1; \text{ and}$$

$$\gamma_2 = -\gamma_1;$$

where:

$\beta_1$ is a view angle at a first x-ray source location;

$\gamma_1$ is a detector angle at the first x-ray source location;

$\beta_2$ is a view angle at a second x-ray source location; and $\gamma_2$ is a detector angle at the second x-ray source location.

8. A method in accordance with claim 1 wherein generating the inconsistency map comprises the step of identifying differences between scan data of each sampling pair.

9. A method in accordance with claim 1 further comprising the step of generating a signal representative of potential partial volume artifacts utilizing the inconsistency map.

10. A method in accordance with claim 9 further comprising transmitting the signal to a control device for varying slice thickness.

11. A system for detecting partial volume artifacts in scan data of an object collected in a tomographic scan, said system configured to:
   identify a sampling pair of the scan data; and
   generate an inconsistency map using the identified sampling pair.

12. A system in accordance with claim 11 further configured to weight the generated inconsistency map.

13. A system in accordance with claim 12 further configured to filter the weighted inconsistency map to generate an initial partial volume signature.

14. A system in accordance with claim 13 wherein to filter the weighted inconsistency map, said system is configured to low pass filter the weighted inconsistency map along a channel direction.

15. A system in accordance with claim 12 further configured to filter the initial partial volume signature to generate a final partial volume signature.

16. A system in accordance with claim 15 wherein to filter the initial partial volume signature, said system is configured to low pass filter the initial partial volume signature.

17. A system in accordance with claim 11 configured to identify the sampling pair in accordance with:

$$\beta_2 = \beta_1 + \pi + 2\gamma_1; \text{ and}$$

$$\beta_2 = -\gamma_1;$$

where:
   $\beta_1$ is a view angle at a first x-ray source location;
   $\gamma_1$ is a detector angle at the first x-ray source location;
   $\beta_2$ is a view angle at a second x-ray source location; and
   $\gamma_2$ is a detector angle at the second x-ray source location.

18. A system in accordance with claim 11 wherein generate the inconsistency map, said system is further configured to identify differences in the scan data of each sampling pair.

19. A system in accordance with claim 11 further configured to generate a signal representative of potential partial volume artifacts utilizing the inconsistency map.

20. A system in accordance with claim 19 further configured to transmit the signal to a control device for varying slice thickness.

* * * * *